(12) United States Patent
Doten et al.

(10) Patent No.: US 6,709,430 B2
(45) Date of Patent: Mar. 23, 2004

(54) ADJUSTABLE FLOW PROBE

(75) Inventors: Gregory P. Doten, Crystal, MN (US);
Thomas A. Tedham, Eden Prairie, MN (US); Brian P. Brockway, Shoreview, MN (US)

(73) Assignee: Transoma Medical, Inc., Arden Hills, MN (US)

( * ) Notice: Subject to any disclaimer, the term of this patent is extended or adjusted under 35 U.S.C. 154(b) by 143 days.

(21) Appl. No.: 09/735,378

(22) Filed: Dec. 12, 2000

(65) Prior Publication Data

US 2002/0072731 A1 Jun. 13, 2002

(51) Int. Cl.⁷ ............................................. A61M 25/16
(52) U.S. Cl. ...................................... 604/533; 604/523
(58) Field of Search ............................ 604/31, 65, 67, 604/253, 533, 523; 600/453–456, 459, 462, 466–467, 465, 504–507; 73/1–16, 1.57, 1.83, 54.11, 54.8, 861 T, 272, 273, 521, 763, 865, 866.5

(56) References Cited

U.S. PATENT DOCUMENTS

| | | | |
|---|---|---|---|
| 3,580,071 A | 5/1971 | Hickman | 73/194 |
| 4,190,057 A | 2/1980 | Hill et al. | 128/675 |
| 4,454,767 A | 6/1984 | Shinkai et al. | 73/861.18 |
| 4,856,321 A * | 8/1989 | Smalling et al. | 73/40.5 A |
| 4,926,875 A | 5/1990 | Rabinovitz et al. | 128/691 |
| 5,318,525 A * | 6/1994 | West et al. | 604/95 |
| 5,487,756 A | 1/1996 | Kallesoe et al. | 607/118 |
| 5,682,899 A * | 11/1997 | Nashef et al. | 128/692 |
| 5,743,270 A * | 4/1998 | Gazzara et al. | 128/724 |
| 6,106,477 A | 8/2000 | Miesel et al. | 600/486 |
| 6,346,080 B1 * | 2/2002 | Wedan et al. | 600/453 |
| 6,354,146 B1 * | 3/2002 | Birchak et al. | 73/61.79 |

FOREIGN PATENT DOCUMENTS

EP 0776640 6/1997 ............. A61F/2/24

OTHER PUBLICATIONS

"Application Brief", *Transonic Systems Inc.*, (Nov. 2000), 1 pg.
"Continuous Cardiac Output", *Transonic Systems Inc.*, (Nov. 2000), 1 pg.

* cited by examiner

*Primary Examiner*—Henry Bennett
*Assistant Examiner*—Nihir Patel
(74) *Attorney, Agent, or Firm*—Schwegman, Lundberg, Woessner & Kluth, P.A.

(57) ABSTRACT

A flow probe has been described which includes a sensor housing and a coupling member. The sensor housing with one or more sensors mated together with the coupling member form the flow probe. The sensor housing accepts a variety of different sized coupling members to form flow probes of different sizes. The sensor housing is adapted to house one or more transducers. Additionally, a version of the flow probe includes strategically located positioning elements for ease in placement and retrieval of the flow probe.

29 Claims, 7 Drawing Sheets

ADJUSTABLE FLOW PROBE

TECHNICAL FIELD

The present invention relates to measurement devices and in particular to flow probes and mechanisms for placement and removal of implantable medical devices.

BACKGROUND INFORMATION

Flow probes are used for measuring the flow of fluid within a conduit. There are many applications in clinical and research medicine in which measurement or estimation of fluid flow within a conduit is desirable. For example, the monitoring of blood flow in a vessel provides information that may be used in a variety of applications. Some of these applications include the discovery and assessment of compounds during the development of various drugs or assessing the hemodynamic status of patients for the purpose of guiding therapies or care. An additional application is the research of the various factors that may impact the hemodymanic status where the blood flow parameter is one of the indicators. For many applications implantable devices such as flow probes are surgically implanted in animals or humans. The placement of flow probes and other implantable devices is a difficult task as the devices are small and precision in placement is vital.

When placing flow probes for measurement of fluid flow within a conduit the orientation of the probe with respect to the conduit is essential. For example, some transit time measurement devices are dependent upon the angle of an ultrasound path with respect to fluid flow. Some flow probes completely encircle or partially encircle the conduit to be monitored and have to be sized properly so as to reduce measurement errors. If the flow probe is not positioned properly measurement errors can result. For example, when a conduit is smaller than the conduit size that a flow probe was designed for, the probe can rotate and/or tilt on the conduit, causing an error in the angle that the ultrasound beam intersects the fluid flow, resulting in an error in the flow measurement.

Flow probes vary in size for the respective application. Currently, individual probes are designed to operate optimally on a single conduit size to reduce the risk of measurement errors caused by ultrasound angle tilting errors. As a result, probes of various sizes must be produced to meet the wide range of applications. The end user has to stock multiple sizes of probes to meet the range of anticipated applications, which is expensive for both the manufacturer and customer.

Accurate placement and, once implanted, proper orientation of flow probes may be difficult to accomplish. Retrieval of implanted devices is also very difficult. Devices such as flow probes are often located in difficult to reach places and accessing the device for removal becomes challenging. Improperly grasping a device with pincers or tweezers may damage the device. In the case of having a memory device that stores calibration or other information integral with the flow probe, the memory device may be damage and information lost due to improper handling with surgical instruments. In other scenarios the device may break up and pieces of the device may be lost within the body cavity.

SUMMARY

The above mentioned problems with medical devices and flow probes are addressed by one or more embodiments of the present invention and will be understood by reading and studying the following specification.

According to one aspect of the present invention an apparatus is provided. The apparatus includes a sensor housing adapted for mounting one or more sensors. The apparatus further includes one of a plurality of different sized coupling members which includes one or more windows for the one or more sensors. The sensor housing is adapted to couple with the one of a plurality of different sized coupling members to accommodate various sized conduits. In one embodiment, the sensor is a transducer and the windows are acoustically transparent windows. Other sensors may be used in the present sensor housing.

According to another aspect of the present invention a flow probe is provided. The flow probe includes one or more transducers and a sensor housing adapted for mounting the one or more transducers. The flow probe also includes one of a plurality of different sized coupling members which includes one or more acoustically transparent windows for the one or more transducers. The sensor housing is adapted to couple with the one of a plurality of different sized coupling members to accommodate various sized conduits.

According to an alternate aspect of the present invention an implantable medical device is provided. The implantable medical device includes a first body. The first body includes positioning elements, such as dimples, for placement and retrieval of the implantable medical device.

DETAILED DESCRIPTION

In the following detailed description, reference is made to the accompanying drawings which form a part hereof, and in which is shown by way of illustration specific embodiments in which the invention may be practiced. It is to be understood that other embodiments may be utilized and structural changes may be made without departing from the scope of the present invention.

Figure 1:
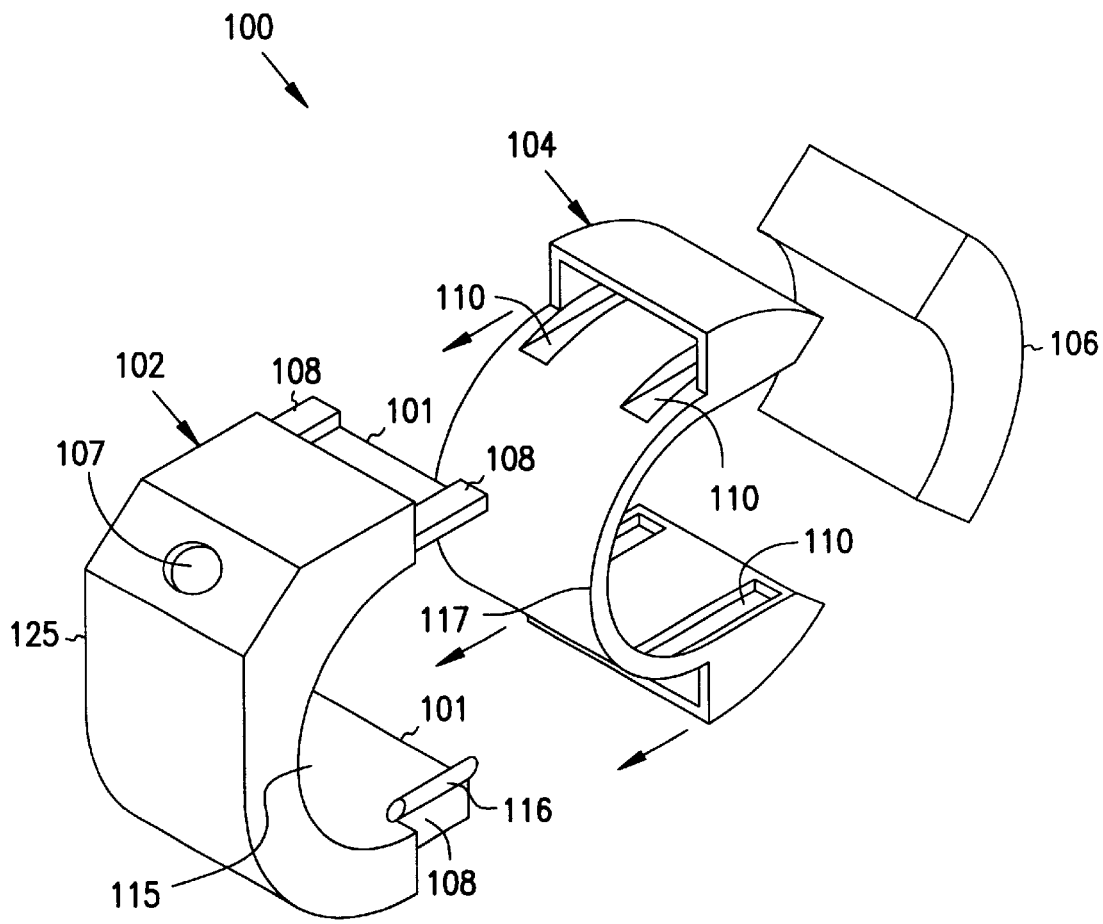
FIG. 1 is an illustration of a flow probe according to one embodiment of the present invention.

FIG. 1 is an illustration of an embodiment of a flow probe shown generally at 100 and constructed according to the teachings of the present invention. The flow probe 100 includes a sensor housing 102 which is adapted to mate or couple with a coupling member 104. When engaged, the outer surface 117 of the coupling member 104 fits snugly against the inner surface 115 of the sensor housing 102.

The sensor housing 102 is adapted to hold one or more sensors. In one embodiment, the sensor is a transducer. The sensor housing includes one or more connecting members 101 extending from the main body 125 of the sensor housing 102. The connecting members 101 engage with slots 110 of the coupling member 104 in order to snugly fit the sensor housing 102 together with the coupling member 104. In one embodiment, the slots 110 also serve as windows for the one or more transducers.

In one embodiment, sensors 116 are secured by holders such as 108 within the sensor housing 102. In one embodiment, the sensor housing accommodates four sensors 116. The sensors are held in precise alignment in order to perform transit-time measurements, flow velocity measurements, and volumetric fluid flow measurements. It is understood that other measurements may be performed without departing from the scope of the present invention. In one embodiment, the holders 108 align the one or more sensors for transit time measurement. In another embodiment, the holders 108, align the one or more sensors for pulse doppler measurement. In a further embodiment, the holders align the one or more sensors for continuous wave doppler measurement.

The coupling member 104 includes one or more windows. In one embodiment, slots 110 also provide windows which are acoustically transparent. Once the sensor housing 102 is coupled with the coupling member 104 transducers 116 mounted within the sensor housing are operable through the acoustically transparent windows in slots 110. In one embodiment, the acoustically transparent windows comprise cut-outs. In one embodiment, the windows comprise a material which separates the sensors from the signal source and which allows the signal to pass through with an acceptable amount of attenuation.

In one embodiment, the sensors 116 are ultrasound transducers which consist of piezoelectric crystals that convert electrical energy to high-power ultrasonic energy. In one embodiment, two crystals in a pair are positioned opposing one another so that they have a common field of view. When mounted on a conduit, these crystals contemporaneously transmit signals through the conduit to be received by the opposite crystal. In another embodiment, two pairs of crystals are used with one crystal in each pair positioned opposing one another so that they have a common field of view. When mounted on a conduit, these crystals transmit signals through the conduit to be received by an opposing crystal. The transducers may be located and/or aligned in any number of ways in order to achieve desired measurements such as transit time, pulse doppler, continuous wave doppler measurements. It is understood that other measurements are possible without departing from the scope of the present invention. It is also understood that the sensor housing is not limited to housing transducers. Furthermore, the number, type and operation of devices which are used may vary without departing from the scope of the present invention.

In one embodiment, the flow probe 100 includes a cable (not shown) which has an access 107. In one embodiment, the flow probe 100 includes a housing release mechanism which allows the sensor housing 102 to be released from the coupling member 104. The sensor housing 102 is removed leaving the coupling member 104 behind.

In one embodiment, the housing release mechanism is a button, which, when depressed, releases sensor housing 102 from coupling member 104. In one embodiment, the housing release mechanism is a release lock. In one embodiment, a tool is used to aid in the release of the sensor housing 102 from the coupling member 104. The tool engages with the sensor housing 102 releases or detaches the sensor housing 102 from the coupling member 104 and enables the sensor housing 102 to be removed.

It is understood that the housing release mechanisms may vary without departing from the scope of the present system.

In one embodiment, the sensor housing 102 is made of a harder durometer material than the coupling member 104. In another embodiment, the coupling member 104 is made of a flexible material which allows the coupling member to conform to a conduit. In one embodiment coupling member 104 and sensor housing 102 are made of the same material. The conduit includes in vivo applications such as a blood vessel, an artery and the like as well as application outside of a living organism such as tubing, channels, tunnels and the like.

In one embodiment, flow probe 100 includes a closure mechanism 106. The closure mechanism 106 allows flow probe 100 to be securely closed about a conduit.

In one embodiment, coupling member 104 includes a closure mechanism 106. The closure mechanism 106 combined with the coupling member 104 provides an apparatus which encircles a conduit. The closure mechanism 106 also provides a stable placement of the sensors in the device with respect to the conduit. In one embodiment, the closure mechanism 106 and coupling member 104 are selected to conform as closely as possible to the conduit without substantially deforming the conduit or restricting the lumen through which fluid is transported.

In one embodiment, the flow probe 100 is designed for use in vivo and one or more of the sensor housing 102, coupling member 104 and the closure mechanism 106 are made of a biocompatible material. Biocompatible materials include materials which are Federal Drug Agency (FDA) or U.S. Pharmacopeia Class VI approved.

In another embodiment, one or more of sensor housing 102, coupling member 104, and/or closure mechanism 106 may be made of a biodegradable material. Biodegradable materials include absorbable synthetic materials, bioabsorbable materials, polyglycolic acid material and/or its copolymers, polyglactin acid material and/or its copolymers, biodegradable polymers or the like. These biodegradable materials allow one or more portions of the probe to decompose within a predetermined time frame.

In one embodiment, a sensor release mechanism is coupled to sensors 116. The sensor release mechanism allows sensors 116 to be removed from sensor housing 102. In one embodiment, the sensor release mechanism is coupled to the sensors and is used to remove the sensors from sensor housing 102 while biodegradable portions such as sensor housing 102 and coupling member 104 of probe 100 remain in vivo. In one embodiment, this provides that the sensor release mechanism can be triggered from a location remote from the probe, allowing the one or more sensors to be released from sensor housing 102. This allows the sensors to be removed from the patient without having to perform a major surgical procedure. In one application of this concept, the biodegradeable portions of the probe biodegrade after approximately 30 days. In one application the probe biodegrades after one week. Other time frames are possible without departing from the scope of the present system.

Figure 2A:
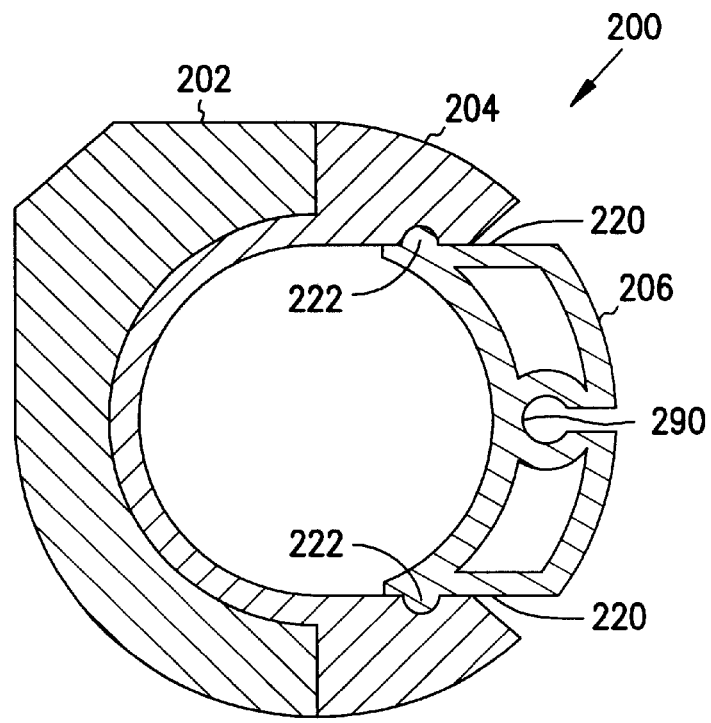
FIG. 2A is a side view of a flow probe constructed according to one embodiment of the present invention.

FIG. 2A is a side view in cross section of one embodiment of a flow probe shown generally at 200 and constructed according to the teachings of the present invention. Flow probe 200 includes a sensor housing 202 and a coupling member 204. FIG. 2A illustrates the sensor housing 202 and coupling member 204 coupled together. The flow probe includes one or more transducers (not shown). Flow probe 200 includes a closure mechanism 206 which is shown secured in place. In one embodiment, closure mechanism 206 is designed with a notch closure mechanism and provides a positive closure. In one embodiment, closure mechanism 206 is shown with protrusions 220 which fit into notches 222 on the coupling member 204.

Figure 2B:
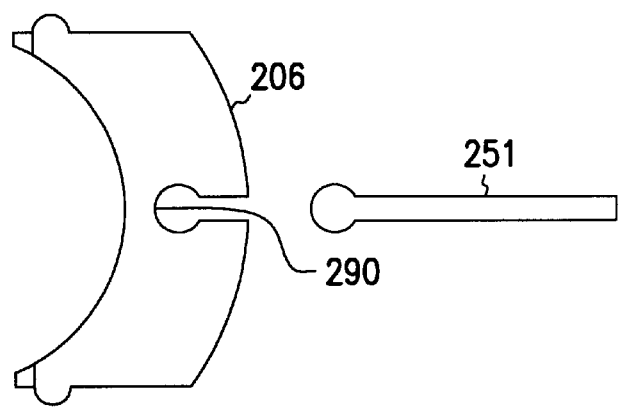
FIG. 2B is a side view of one embodiment of a tool for placement and retrieval of one embodiment of a closure mechanism.

In operation, one embodiment of closure mechanism 206 is snapped in place by inserting one of the two protrusions 220 into one of the two notches 222 in the coupling member and then snapping the second protrusion 220 into the second notch 222. In one embodiment, closure mechanism 206 includes a receptacle 290 which receives a positioning tool 251 as shown in FIG. 2B. The tool is used to place the closure mechanism 206 in position with respect to the coupling member 204 and to snap closure mechanism 206 into place. In one embodiment, the receptacle 290 may aid in deforming the closure mechanism 206 to snap into place.

In another embodiment, closure mechanism 206 slides into place using the notches 222 as guides for the protrusions 220. Closure mechanism 206 is adapted to slide into coupling member 204 from the left side of the coupling member 204 or from the right side of the coupling member 204. Receptacle 290 is also useful for sliding closure mechanism 206 into place using its mating positioning tool (not shown).

Figure 3:
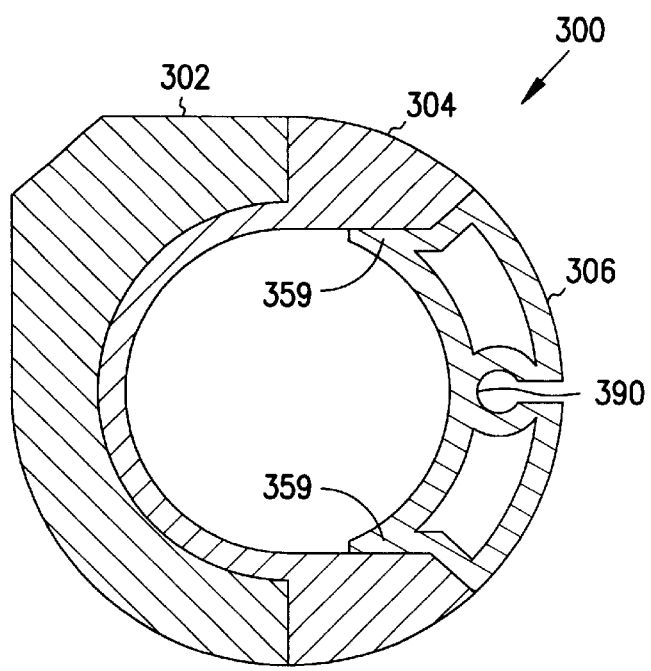
FIG. 3 is a side view of a flow probe constructed according to one embodiment of the present invention.

FIG. 3 is a side view in cross section of another embodiment of a flow probe shown generally at 300 and constructed according to the teachings of the present invention. Flow probe 300 includes a sensor housing 302 and a coupling member 304 which are shown coupled together. Flow probe 300 also includes a closure mechanism 306. Closure mechanism 306 is designed as a sliding closure mechanism and provides a positive closure.

In operation, one embodiment of closure mechanism 306 slides into place with the coupling member 304 to form a positive closure about a conduit. Closure mechanism 306 slides into place without the need for notches on the coupling member to guide the closure mechanism. In one embodiment, closure mechanism 306 includes extensions 359 which are shaped to conform to coupling member 304 and aid in sliding closure mechanism 306 in place. Closure mechanism 306 is adapted to slide into coupling member 304 from the left side of the coupling member 304 or from the right side of the coupling member 304.

In another embodiment, closure mechanism 306 is snapped in place by placing one of the two extensions 359 into place on the coupling member 304 and then snapping the second extrusion 359 into place on the coupling member 304. In one embodiment, closure mechanism 306 includes a receptacle 390 which receives a positioning tool (not shown) for placement of the closure mechanism 306. In one embodiment, the receptacle 390 may aid in deforming the closure mechanism 306 to snap into place.

Figure 4:
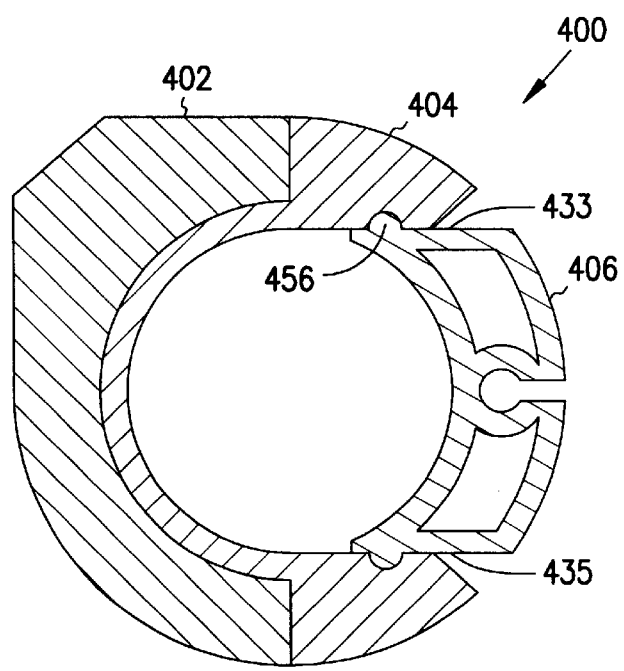
FIG. 4 is a side view of a flow probe constructed according to one embodiment of the present invention.

FIG. 4 is also a side view in cross section of another embodiment of a flow probe shown generally at 400 and constructed according to the teachings of the present invention. Flow probe 400 includes a sensor housing 402 and a coupling member 404 which are shown coupled together. Flow probe 400 includes a closure mechanism 406. Closure mechanism 406 is designed as a rotating closure and is secured at one end.

In operation, closure mechanism 406 is secured in place at a first end 433 using a hinge 456. In one embodiment, the closure mechanism is secured at first end 433 using a post. In one embodiment, the closure mechanism is secured at first end 433 using a screw. In one embodiment, the closure mechanism is secured at first end 433 using a rivet. In one embodiment, the closure mechanism is secured at first end 433 using a knob. Other securing apparatus and method may be employed without departing from the scope of the present invention. The first end 433 of closure mechanism 406 rotates about the hinge 456 and swings the second end 435 into place to provide a positive closure.

It is understood that closure mechanism 106 of FIG. 1 is not limited by closure mechanisms 206, 306 and 406 of FIGS. 2, 3, and 4, respectively. One of ordinary skill in the art understands that any number of closure mechanisms which provide a positive closure may be substituted for these closures. In one embodiment, closure mechanism 206, 306 and 406 each include a locking device (not shown) which allows the closure mechanism to lock into place. In one embodiment, closure mechanism 106 is omitted and flow probe 100 is secured to a conduit such as a vessel using a tissue adhesive or other attaching means.

Figure 5A:
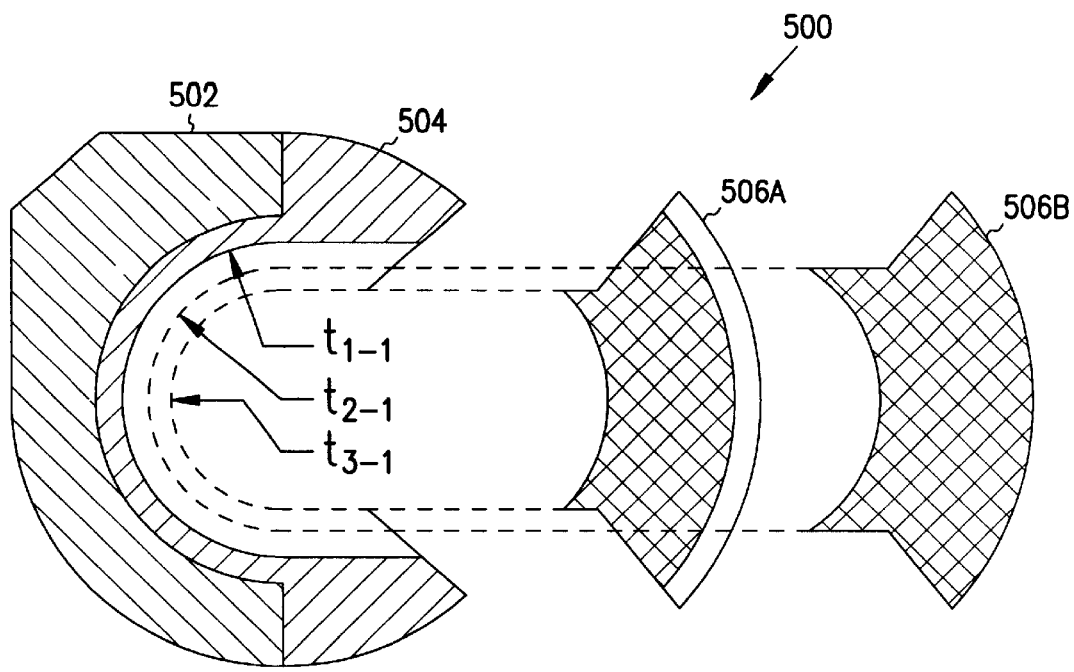
FIG. 5A is an illustration of a flow probe constructed according to one embodiment of the present invention.

FIG. 5A is an illustration of one embodiment of a flow probe indicated generally at 500 and constructed according to the teachings of the present invention. Flow probe 500 includes a sensor housing 502 and a coupling member 504. In addition flow probe 500 includes one or more transducers (not shown). FIG. 5A illustrates the sensor housing 502 coupled together with coupling member 504. The sensor housing 502 is adapted to couple with a variety of different sized coupling members 504 in order to form flow probes of selected sizes. The coupling members 504 are interchangeable with the sensor housing 502. As shown in FIG. 5A, coupling member 504 has a thickness t1-1. As illustrated with the dashed lines the sensor housing is adapted to couple with a coupling member of any appropriate thickness e.g. t2-1, t3-1. Other sizes and geometries may be used without departing from the scope of the present invention.

Thus, a single sensor housing 502 is adapted to couple with a variety of different sized coupling members 504 to accommodate various sized conduits. In one embodiment, flow probe 500 includes a closure mechanism 506A to match a particular coupling member 504 to allow the flow probe to encircle a particular conduit. Another closure mechanism 506B may also be used with a different sized coupling member 504 to achieve a close fit to a conduit. An accurate fit reduces movement of the apparatus about the conduit and may improve overall measurement accuracy.

Figure 5B:
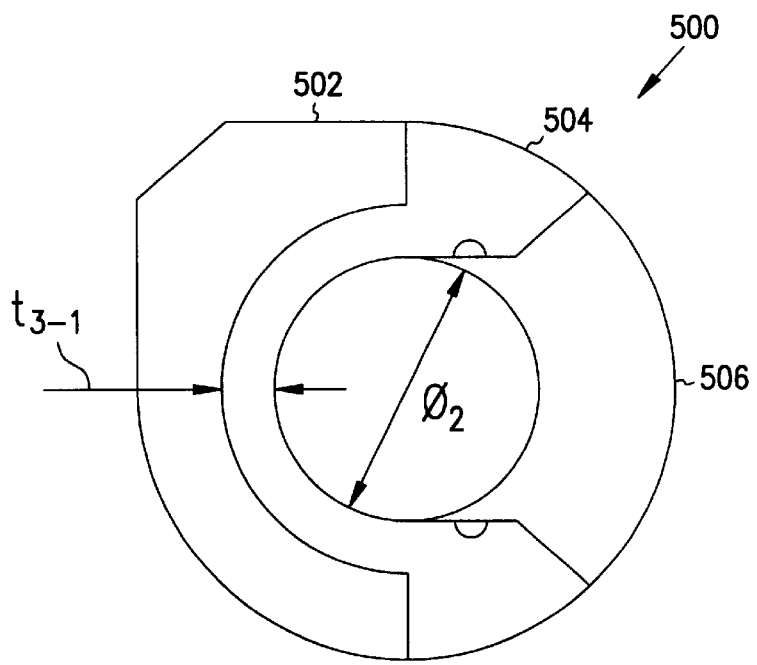
FIG. 5B is an illustration of a flow probe constructed according to one embodiment of the present invention.

FIG. 5B shows one embodiment of a flow probe 500 with a particular coupling member 504 attached to sensor housing 502 and a particular closure mechanism 506. Different sized conduits may be accommodated using the different sized components, as demonstrated by FIG. 5B. For example, in one embodiment a conduit with an outer diameter of approximately $\varnothing_2$ may be accommodated. In one embodiment, a conduit with an outer diameter of approximately $\varnothing_2$ or smaller may be accommodated. In one embodiment, a conduit with an outer diameter of approximately 75% of $\varnothing_2$ to approximately 100% of $\varnothing_2$ may be accommodated. It is understood that other sizes and shapes of coupling members and closure mechanisms may be used without departing from the scope of the present invention.

Figure 6A:
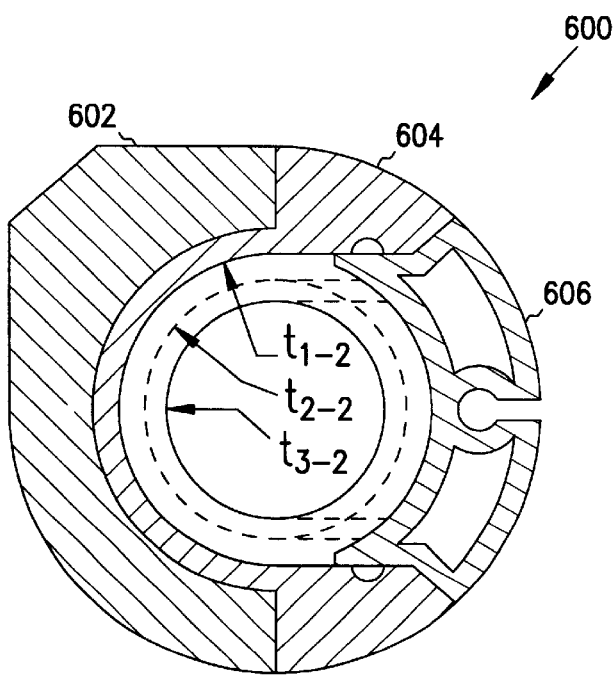
FIG. 6A is an illustration of a flow probe constructed according to one embodiment of the present invention.

FIG. 6A is an illustration of an embodiment of a flow probe indicated generally at 600 and constructed according to the teachings of the present invention. Flow probe 600 includes sensor housing 602, coupling member 604 and a closure mechanism 606. In addition flow probe 600 includes one or more transducers (not shown). FIG. 6A illustrates the sensor housing 602 coupled to coupling member 604. The sensor housing 602 is adapted to couple with a variety of different sized coupling members 604 and closure mechanisms 606 in order to form different sized flow probes. As shown in FIG. 6A, coupling member 604 has a thickness t1-2. As illustrated with the dashed lines, the sensor housing is adapted to couple with a coupling member of any appropriate thickness e.g. t2-2 and t3-2. For example, in one embodiment a conduit with an outer diameter of approximately $\phi_2$ may be accommodated. In one embodiment, a conduit with an outer diameter of approximately $\phi_2$ or smaller may be accommodated. In one embodiment, a conduit with an outer diameter of approximately 75% of $\phi_2$ to approximately 100% of $\phi_2$ may be accommodated. In various embodiments, both the coupling member 604 and the closure mechanism 606 vary in thickness and geometries to accommodate various sized conduits, without departing from the scope of the present invention.

Figure 6B:
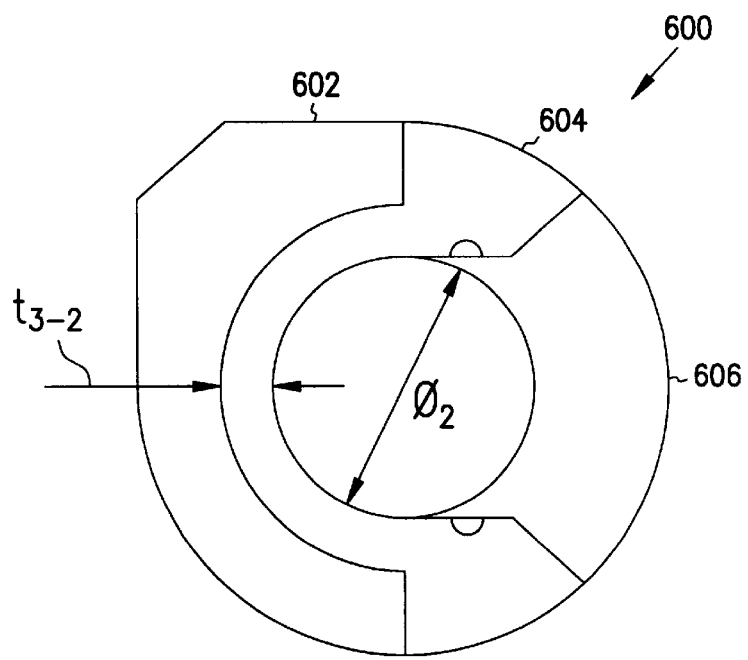
FIG. 6B is an illustration of a flow probe constructed according to one embodiment of the present invention.

FIG. 6B demonstrates flow probe 600 with transducer housing 602 with thickness t3-2. It is understood that other shapes and sizes may be used without departing from the scope of the present invention.

Figure 7:
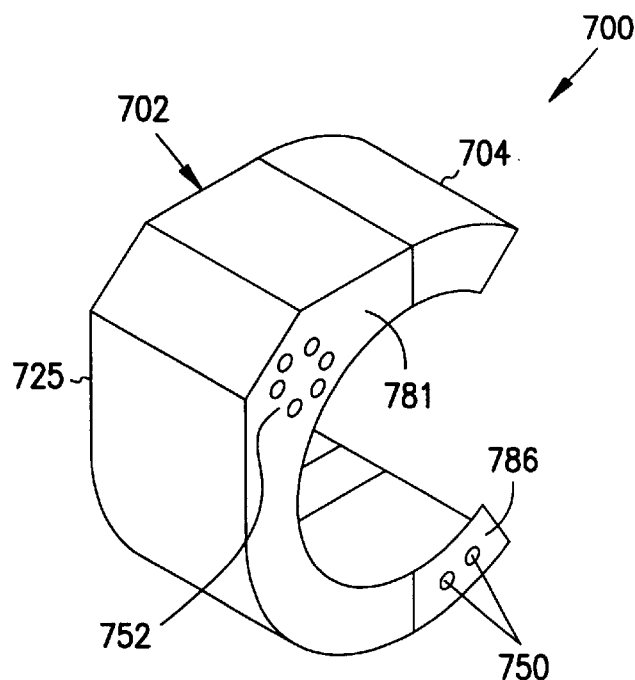
FIG. 7 is an illustration of a flow probe constructed according to one embodiment of the present invention.

FIG. 7 is an illustration of an embodiment of a flow probe indicated generally at 700 and constructed according to the teachings of the present invention. Flow probe 700 includes sensor housing 702 coupled to coupling member 704. In one embodiment, flow probe 700 includes a closure mechanism (not shown) which provides the flow probe positive closure about a conduit. Flow probe 700 has positioning elements. The positioning elements include means for positioning the flow probe 700. One example of positioning elements includes a pair of dimples 750 on the left face 786 and another pair of dimples (not shown) on the right face of coupling member 704. Dimples 750 are used to assist in placement and retrieval of the flow probe 700 or coupling member 704. A tool such as a clamp, tweezers, pincers, forceps or the like with protrusions which mate with dimples 750 and the dimples not shown on the right face is used to pick up, place or retrieve a device such as flow probe 700. In addition, the main body 725 of flow probe 700 has a first set of dimples 752 and a second set of dimples (not shown) which assist in grasping the flow probe 700 for placement and retrieval of flow probe 700. In this embodiment, the dimples are placed on surface 781 and on an opposing surface (not shown) to allow the flow probe to be grasped in a plurality of orientations. In other embodiments, the dimples are placed in pairs, in a radial set, and in rows. It is understood that other positioning elements may be used without departing from the scope of the present invention. For example, other dimple designs and placements may be used without departing from the scope of the present invention. The dimples are located so as to assist in grasping the flow probe 700 using a tool such as a pair of forceps or a clamp with protrusions which mate with dimples 752 or 750.

Figure 8:
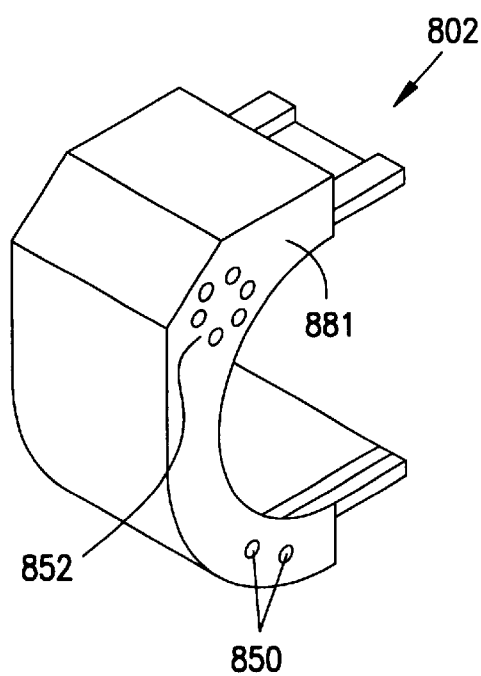
FIG. 8 is an illustration of a sensor housing for a flow probe constructed according to one embodiment of the present invention.

FIG. 8 is an illustration of one embodiment of a sensor housing for a flow probe indicated generally at 802 and constructed according to the teachings of the present invention. The sensor housing 802 includes a pair of dimples 850 on the left face 881 and another pair of dimples (not shown) on the right face. In addition, sensor housing 802 includes a first radial set of dimples 852 on a first face 881 of sensor housing 802 and a second radial set of dimples (not shown) on a second face of sensor housing 802.

The dimples placed on sensor housing 802 mate with a tool which allows the flow probe and its components to be picked up, placed and removed with ease. In one embodiment, the tool attaches to any two opposing pairs of dimples for grasping the flow probe, picking up, placing, retrieving sensor housing 802 and the like.

Figure 9:
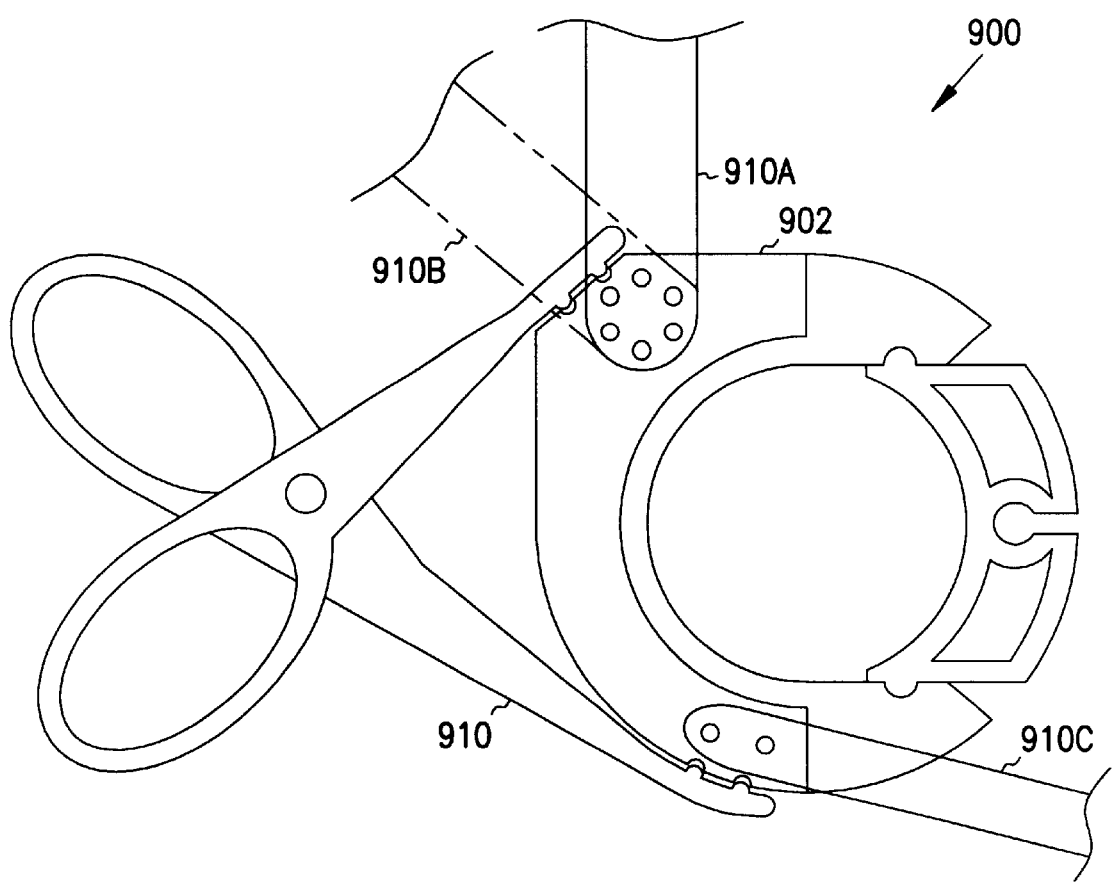
FIG. 9 is an illustration of a flow probe and tool according to one embodiment of the present invention.

FIG. 9 is an illustration of one embodiment of a flow probe 900 constructed according to the teachings of the present invention. Flow probe 900 is illustrated with a tool 910 grasping sensor housing 902 of probe 900. (Note: The tool is not shown drawn to scale) Although FIG. 9 shows the tool 910 grasping sensor housing 902 in a first example, it is not limited to this attachment location. For example, tool 910 may grasp dimples on the side of the sensor housing 902, as shown by example 910A. Another position of the tool 910 is shown at example 910B. Yet another example is shown in example 910C. It is understood that in other embodiments the positioning, number and type of dimples may vary without departing from the scope of the present invention. For example, the dimples may be placed on the sensor housing, the coupling member or both the sensor housing and the coupling member. As a further example, in alternate embodiments, the dimples may be square or triangular in shape. As a further example, it is understood that an alternate tool for grasping a flow probe may be employed and that neither the dimples nor the tools shown are meant to be limiting. For example, slots, grooves, bumps and the like may be used to mate with a tool for placement and retrieval of the flow probe and its components. In one embodiment, the tool is also designed to attach to and release the sensor housing from the coupling member. This allows retrieval of the sensor housing with transducers and leaves the coupling member with closure mechanism in place.

It is understood that in different embodiments positioning elements may be located on one or more of the sensor housing, the coupling member, and the closure mechanism. Different combinations of placement of the positioning elements are possible without departing from the scope of the present teachings. In one embodiment, the closure mechanism is positioned using positioning elements. In one embodiment, the coupling member is positioned using positioning elements. In one embodiment, the coupling members are interchanged using positioning elements and tools as demonstrated in the present patent application. In one embodiment, the closure mechanism is positioned, inserted or removed using tools according to the teachings of the present patent application. One aspect of positioning elements and tools on the various components allows for positioning and assembly of the flow probe while in the body. The different positioning elements discussed herein may be used in various combinations without departing from the scope of the present description.

The sensor housing, flow probes and components of flow probes illustrated in FIGS. 1–9 are not meant to be exhaustive. One of ordinary skill in the art will understand that the flow probes and components may be of any size, shape and/or style appropriate for a particular application. In one embodiment, a flow probe which completely encircles a conduit is used. In another embodiment, a flow probe which partially encircles a conduit is used. In an alternate embodiment, a flow probe which conforms to the shape a conduit and either completely encircles or partially encircles the conduit is used.

CONCLUSION

An apparatus which includes a sensor housing adapted for mounting one or more sensors has been described. The apparatus further includes one of a plurality of different sized coupling members which includes one or more acoustically transparent windows for the one or more transducers. The sensor housing is adapted to couple with one of the plurality of different sized coupling members to accommodate various sized conduits.

In addition, a flow probe has been described. The flow probe includes one or more transducers and a sensor housing adapted for mounting the one or more transducers. The flow probe also includes one of a plurality of different sized coupling members which includes one or more acoustically transparent windows for the one or more transducers. The sensor housing is adapted to couple with the one of a plurality of different sized coupling members to accommodate various sized conduits.

Further an implantable medical device has been described. The implantable medical device includes a first body. The first body includes strategically located dimples for placement and retrieval of the implantable medical device.

Although specific embodiments have been illustrated and described herein, it will be appreciated by those of ordinary skill in the art that any arrangement which is calculated to achieve the same purpose may be substituted for the specific embodiment shown. For example, one of ordinary skill in the art would understand that dimples could be used with any other appropriate implantable device, e.g., a transmitter, a catheter, a pacemaker or defibrillator and the like. This application is intended to cover any adaptations or variations of the present invention. Therefore, it is intended that this invention be limited only by the claims and the equivalents thereof.

What is claimed is:

1. An apparatus for holding one or more sensors for measurement of fluid flow in a conduit, comprising:
    a sensor housing adapted for mounting the one or more sensors and adapted to partially surround the conduit;
    one of a plurality of different sized coupling members adapted to partially surround the conduit, including one or more windows through which the one or more sensors measure fluid flow in the conduit; and
    wherein the sensor housing is adapted to receive and couple with the one of a plurality of different sized coupling members to accommodate various sized conduits.

2. The apparatus of claim 1, wherein the sensor housing comprises a main body and at least one connecting member extending from the main body, wherein each of the at least one connecting member is adapted to hold the one or more sensors.

3. The apparatus of claim 1, wherein the one of a plurality of different sized coupling members conforms to a conduit.

4. The apparatus of claim 2, wherein the main body of the sensor housing includes a housing release mechanism, wherein the housing release mechanism is adapted to detach the sensor housing from the one of a plurality of different sized coupling members once they are coupled together.

5. The apparatus of claim 1, further comprising a closure mechanism coupleable to the one of a plurality of different sized coupling members.

6. The apparatus of claim 5, wherein the sensor housing, the one of a plurality of different sized coupling members, and the closure mechanism are each made of a biocompatible material.

7. The apparatus of claim 6, wherein the sensor housing, the one of a plurality of different sized coupling members, and the closure mechanism are each made of a biodegradable material.

8. The apparatus of claim 7, further comprising a sensor release mechanism for releasing the one or more sensors from the sensor housing, wherein the one or more sensors are removable leaving the biodegradable material in vivo.

9. The apparatus of claim 1, wherein the sensor housing is made of a harder durometer material than the one of a plurality of different sized coupling members.

10. The apparatus of claim 2, wherein the main body of the sensor housing includes positioning elements to aid in placement and retrieval of the sensor housing.

11. The apparatus of claim 10, wherein the positioning elements comprise a first array of dimples and a second array of dimples.

12. The apparatus of claim 11, wherein the first array of dimples and the second array of dimples comprise a circular pattern.

13. The apparatus of claim 10, wherein the main body of the sensor housing further includes a housing release mechanism, wherein the housing release mechanism is adapted to detach the sensor housing from the one of a plurality of different sized coupling members once they are coupled together.

14. The flow probe of claim 10, wherein the one or more sensors are one or more ultrasound transducers and the one or more windows are acoustically transparent.

15. The flow probe of claim 14, wherein the one or more ultrasound transducers comprise one or more piezoelectric transducers.

16. The apparatus of claim 1, wherein the one or more sensors are ultrasound transducers and the one or more windows are acoustically transparent.

17. An apparatus for holding one or more sensors for measurement of fluid flow in a conduit, comprising:
    a coupling member for a flow probe, wherein the coupling member is adapted to partially surround the conduit and be received by a sensor housing for the flow probe, wherein the sensor housing is adapted for mounting the one or more sensors and is adapted to partially surround the conduit;
    and wherein the coupling member includes one or more windows through which the one or more sensors measure fluid flow in the conduit.

18. The apparatus of claim 17, further comprising a closure mechanism coupleable to the coupling member.

19. The apparatus of claim 18, wherein the coupling member and the closure mechanism are made of a biocompatible material.

20. The apparatus of claim 18, wherein the coupling member and the closure mechanism are made of a biodegradable material.

21. The apparatus of claim 17, wherein the one or more windows are transparent to the one or more sensors.

22. A sensor housing for a flow probe to hold one or more sensors, comprising:
    a main body adapted to mate with one of a plurality of different sized coupling members to partially surround various sized conduits;
    at least one connecting member extending from the main body, each of the at least one connecting members is adapted to hold the one or more sensors; and
    wherein the one of a plurality of different sized coupling members includes one or more windows for the one or more sensors.

23. The sensor housing of claim 22, wherein the main body and the at least one connecting member are each made of a biocompatible material.

24. The sensor housing of claim 22, wherein the one or more sensors are one or more transducers and the one or more windows are acoustically transparent.

25. An apparatus for holding one or more sensors for measurement of fluid flow in a conduit, comprising:

a sensor housing adapted for mounting one or more sensors, the sensor housing being adapted to partially surround the conduit;

two or more coupling members, wherein each of the two or more coupling members includes one or more windows for the one or more sensors, each of the two or more coupling members being adapted to partially surround the conduit; and wherein the sensor housing is adapted to receive and couple with the two or more coupling members to accommodate various sized conduits in which the sensor housing receives and couples with a first coupling member to accommodate a first conduit size and a second coupling member to accommodate a second conduit size.

26. The apparatus of claim 25, further comprising a closure mechanism coupleable to at least one of the two or more coupling members to provide a positive closure.

27. The apparatus of claim 26, wherein the sensor housing, the two or more coupling members, and the closure mechanism are each made of a biocompatible material.

28. The apparatus of claim 27, wherein the two or more coupling members are made of a biodegradable material.

29. The apparatus of claim 25, wherein the one or more sensors are transducers and the one or more windows are acoustically transparent.

* * * * *